(12) United States Patent
Ghione et al.

(10) Patent No.: US 8,057,539 B2
(45) Date of Patent: Nov. 15, 2011

(54) SYSTEM FOR IN SITU POSITIONING OF CARDIAC VALVE PROSTHESES WITHOUT OCCLUDING BLOOD FLOW

(75) Inventors: Laura Ghione, Turin (IT); Giovanni Righini, Chivasso-Torino (IT); Eric Manasse, Milan (IT); Giovanni Rolando, Chavasso-Torino (IT); Paolo Gaschino, Castagneto Po-Torino (IT); Dong Ik Shin, Poway, CA (US)

(73) Assignee: Sorin Biomedica Cardio S.r.l., Saluggia (Vercelli) (IT)

( * ) Notice: Subject to any disclaimer, the term of this patent is extended or adjusted under 35 U.S.C. 154(b) by 315 days.

(21) Appl. No.: 11/612,974

(22) Filed: Dec. 19, 2006

(65) Prior Publication Data

US 2008/0147160 A1    Jun. 19, 2008

(51) Int. Cl.
  *A61F 2/24* (2006.01)
(52) U.S. Cl. ...................................... 623/2.11
(58) Field of Classification Search ................ 623/2.11, 623/1.11–1.12; 604/103.07, 509; 606/113, 606/114, 127, 159, 191–198, 200
See application file for complete search history.

(56) References Cited

U.S. PATENT DOCUMENTS

| | | | |
|---|---|---|---|
| 3,671,979 A | 6/1972 | Moulopoulos | |
| 4,011,947 A | 3/1977 | Sawyer | |
| 4,056,854 A | 11/1977 | Boretos et al. | |
| 4,477,930 A | 10/1984 | Totten et al. | |
| 4,601,706 A | 7/1986 | Aillon | |
| 4,624,822 A | 11/1986 | Arru et al. | |
| 4,684,364 A | 8/1987 | Sawyer et al. | |
| 4,722,725 A | 2/1988 | Sawyer et al. | |
| 4,732,152 A | 3/1988 | Wallsten et al. | |
| 4,758,151 A | 7/1988 | Arru et al. | |
| 4,777,951 A | 10/1988 | Cribier et al. | |
| 4,784,644 A | 11/1988 | Sawyer et al. | |
| 4,994,077 A | 2/1991 | Dobben | |
| 5,084,151 A | 1/1992 | Vallana et al. | |
| 5,123,919 A | 6/1992 | Sauter et al. | |
| 5,133,845 A | 7/1992 | Vallana et al. | |
| 5,181,911 A * | 1/1993 | Shturman | 604/103.07 |
| 5,201,757 A | 4/1993 | Heyn et al. | |
| 5,287,848 A | 2/1994 | Cubb et al. | |

(Continued)

FOREIGN PATENT DOCUMENTS

DE      195 46 692      6/1997

(Continued)

OTHER PUBLICATIONS

European Search Report and Search Opinion of European Patent Application No. 07115960.2, dated Jan. 24, 2008.

(Continued)

*Primary Examiner* — Melanie Tyson
*Assistant Examiner* — Son Dang
(74) *Attorney, Agent, or Firm* — Faegre & Benson LLP

(57) ABSTRACT

An instrument for positioning a cardiac valve prosthesis in a vessel includes a wire element to slidingly guide the valve prosthesis towards an implantation site and an expandable element coupled to the wire element. The expandable element is expandable in the vessel to position the wire element in association with the implantation site. A method for positioning a cardiac valve prosthesis includes securing a delivery instrument at an appropriate location at the implantation site and delivering the valve prosthesis to the implantation site using the delivery instrument.

13 Claims, 5 Drawing Sheets

U.S. PATENT DOCUMENTS

| | | |
|---|---|---|
| 5,304,189 A | 4/1994 | Goldberg et al. |
| 5,332,402 A | 7/1994 | Teitelbaum |
| 5,370,684 A | 12/1994 | Vallana et al. |
| 5,370,685 A | 12/1994 | Stevens |
| 5,387,247 A | 2/1995 | Vallana et al. |
| 5,397,351 A | 3/1995 | Pavcnik et al. |
| 5,411,552 A | 5/1995 | Andersen et al. |
| 5,423,886 A | 6/1995 | Arru et al. |
| 5,445,646 A | 8/1995 | Euteneuer et al. |
| 5,545,214 A | 8/1996 | Stevens |
| 5,554,185 A | 9/1996 | Block et al. |
| 5,556,414 A | 9/1996 | Turi |
| 5,662,712 A | 9/1997 | Pathak et al. |
| 5,693,083 A | 12/1997 | Baker et al. |
| 5,766,151 A | 6/1998 | Valley et al. |
| 5,772,693 A | 6/1998 | Brownlee |
| 5,824,064 A | 10/1998 | Taheri |
| 5,840,081 A | 11/1998 | Andersen et al. |
| 5,849,005 A | 12/1998 | Garrison et al. |
| 5,855,597 A | 1/1999 | Bessler et al. |
| 5,855,601 A | 1/1999 | Jayaraman |
| 5,871,489 A | 2/1999 | Ovil |
| 5,925,063 A | 7/1999 | Khosravi |
| 5,951,600 A | 9/1999 | Lemelson |
| 5,954,766 A | 9/1999 | Zadno-Azizi et al. |
| 5,957,949 A | 9/1999 | Leonhardt et al. |
| 5,980,570 A | 11/1999 | Simpson |
| 6,010,530 A | 1/2000 | Goicoechea |
| 6,010,531 A | 1/2000 | Donlon et al. |
| 6,029,671 A | 2/2000 | Stevens et al. |
| 6,030,360 A | 2/2000 | Biggs |
| 6,106,497 A | 8/2000 | Wang |
| 6,125,852 A | 10/2000 | Stevens et al. |
| 6,139,572 A | 10/2000 | Campbell et al. |
| 6,168,614 B1 | 1/2001 | Andersen et al. |
| 6,251,093 B1 | 6/2001 | Valley et al. |
| 6,299,638 B1 | 10/2001 | Sauter |
| 6,309,382 B1 | 10/2001 | Garrison et al. |
| 6,346,071 B1 | 2/2002 | Mussivand |
| 6,402,780 B2 | 6/2002 | Williamson, IV et al. |
| 6,416,474 B1* | 7/2002 | Penner et al. ............... 600/309 |
| 6,425,916 B1* | 7/2002 | Garrison et al. ............ 623/2.11 |
| 6,454,799 B1 | 9/2002 | Schreck |
| 6,458,153 B1 | 10/2002 | Bailey et al. |
| 6,482,228 B1 | 11/2002 | Norred |
| 6,572,642 B2 | 6/2003 | Rinaldi et al. |
| 6,582,462 B1 | 6/2003 | Andersen et al. |
| 6,607,553 B1 | 8/2003 | Healy et al. |
| 6,641,558 B1 | 11/2003 | Aboul-Hosn et al. |
| 6,645,197 B2 | 11/2003 | Garrison et al. |
| 6,652,578 B2 | 11/2003 | Bailey et al. |
| 6,685,739 B2 | 2/2004 | DiMatteo et al. |
| 6,726,648 B2 | 4/2004 | Kaplon et al. |
| 6,726,712 B1 | 4/2004 | Raeder-Devens et al. |
| 6,730,118 B2 | 5/2004 | Spenser et al. |
| 6,733,525 B2 | 5/2004 | Yang et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,830,584 B1 | 12/2004 | Seguin |
| 6,830,585 B1 | 12/2004 | Artof et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,913,618 B2 | 7/2005 | Denardo et al. |
| 6,945,957 B2 | 9/2005 | Freyman |
| 6,964,673 B2* | 11/2005 | Tsugita et al. ............... 606/200 |
| 6,974,464 B2 | 12/2005 | Quijano et al. |
| 6,981,942 B2 | 1/2006 | Khaw et al. |
| 6,991,646 B2 | 1/2006 | Clerc et al. |
| 7,001,423 B2 | 2/2006 | Euteneuer et al. |
| 7,018,406 B2 | 3/2006 | Seguin et al. |
| 7,018,408 B2 | 3/2006 | Bailey et al. |
| 7,041,132 B2 | 5/2006 | Quijano et al. |
| 7,044,966 B2 | 5/2006 | Svanidze et al. |
| 7,077,801 B2 | 7/2006 | Haverich |
| 7,101,396 B2 | 9/2006 | Artof et al. |
| 7,144,364 B2 | 12/2006 | Barbut et al. |
| 7,156,872 B2 | 1/2007 | Strecker |
| 7,195,641 B2 | 3/2007 | Palmaz et al. |
| 7,201,761 B2 | 4/2007 | Woolfson et al. |
| 7,329,279 B2 | 2/2008 | Haug et al. |
| 7,338,467 B2 | 3/2008 | Lutter |
| 7,338,520 B2 | 3/2008 | Bailey et al. |
| 7,374,571 B2 | 5/2008 | Pease et al. |
| RE40,377 E | 6/2008 | Williamson, IV et al. |
| 7,399,315 B2 | 7/2008 | Iobbi |
| 7,544,206 B2 | 6/2009 | Cohn |
| 7,556,646 B2 | 7/2009 | Yang et al. |
| 7,618,432 B2 | 11/2009 | Pedersen et al. |
| 7,708,775 B2 | 5/2010 | Rowe et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0039450 A1 | 11/2001 | Pavcnik et al. |
| 2001/0044591 A1 | 11/2001 | Stevens et al. |
| 2002/0029075 A1 | 3/2002 | Leonhardt |
| 2002/0042651 A1 | 4/2002 | Liddicoat et al. |
| 2002/0045846 A1 | 4/2002 | Kaplon et al. |
| 2002/0058995 A1 | 5/2002 | Stevens |
| 2002/0099431 A1 | 7/2002 | Armstrong et al. |
| 2002/0107531 A1 | 8/2002 | Schreck et al. |
| 2002/0117264 A1 | 8/2002 | Rinaldi et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033000 A1 | 2/2003 | DiCaprio et al. |
| 2003/0036795 A1 | 2/2003 | Andersen et al. |
| 2003/0055495 A1 | 3/2003 | Pease et al. |
| 2003/0109924 A1 | 6/2003 | Cribier |
| 2003/0130729 A1 | 7/2003 | Paniagua et al. |
| 2003/0153974 A1 | 8/2003 | Spenser et al. |
| 2003/0163194 A1 | 8/2003 | Quijano et al. |
| 2003/0191521 A1 | 10/2003 | Denardo et al. |
| 2003/0191528 A1 | 10/2003 | Quijano et al. |
| 2004/0034411 A1 | 2/2004 | Quijano et al. |
| 2004/0039371 A1 | 2/2004 | Tockman et al. |
| 2004/0039436 A1 | 2/2004 | Spenser et al. |
| 2004/0039442 A1 | 2/2004 | St. Goar et al. |
| 2004/0049266 A1 | 3/2004 | Anduiza et al. |
| 2004/0055606 A1 | 3/2004 | Hendricksen et al. |
| 2004/0078072 A1 | 4/2004 | Tu et al. |
| 2004/0093060 A1 | 5/2004 | Seguin et al. |
| 2004/0093063 A1 | 5/2004 | Wright et al. |
| 2004/0106976 A1 | 6/2004 | Bailey et al. |
| 2004/0127848 A1 | 7/2004 | Freyman |
| 2004/0147993 A1 | 7/2004 | Westlund et al. |
| 2004/0215333 A1 | 10/2004 | Duran et al. |
| 2004/0236170 A1 | 11/2004 | Kim |
| 2004/0249413 A1 | 12/2004 | Allen et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Salahieh et al. |

| | | |
|---|---|---|
| 2005/0137693 A1 | 6/2005 | Salahieh et al. |
| 2005/0137694 A1 | 6/2005 | Salahieh et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bjarne |
| 2005/0251251 A1 | 11/2005 | Cribier |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1* | 8/2006 | Stacchino et al. ............ 623/2.18 |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen et al. |
| 2006/0271081 A1 | 11/2006 | Realyvasquez |
| 2006/0276775 A1 | 12/2006 | Rosenberg et al. |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtain |
| 2007/0118207 A1 | 5/2007 | Amplatz et al. |
| 2007/0118209 A1 | 5/2007 | Strecker |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Strommer et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1 | 7/2010 | Alkhatib |
| 2010/0292782 A1 | 11/2010 | Giannetti |
| 2010/0292783 A1 | 11/2010 | Giannetti |
| 2010/0292784 A1 | 11/2010 | Giannetti |

FOREIGN PATENT DOCUMENTS

| | | |
|---|---|---|
| DE | 198 57 887 | 7/2000 |
| EP | 0 133 420 | 2/1988 |
| EP | 0155245 B1 | 5/1990 |
| EP | 0 592 410 | 10/1995 |
| EP | 0 592 410 B1 | 10/1995 |
| EP | 0 512 359 | 12/1996 |
| EP | 0515324 B1 | 12/1996 |
| EP | 0 850 607 | 7/1998 |
| EP | 1 057 460 | 12/2000 |
| EP | 1 088 529 | 4/2001 |
| EP | 1356793 | 10/2003 |
| EP | 1356793 A2 | 10/2003 |
| EP | 0 852 481 B1 | 2/2004 |
| EP | 1440671 A2 | 7/2004 |
| EP | 0 955 895 B1 | 8/2005 |
| EP | 1 488 735 B1 | 6/2007 |
| EP | 1212989 B1 | 1/2008 |
| EP | 1 653 884 B1 | 6/2008 |
| EP | 1935377 A1 | 6/2008 |
| EP | 1 955 643 A1 | 8/2008 |
| EP | 1570809 B1 | 1/2009 |
| EP | 2033581 A1 | 3/2009 |
| EP | 2033597 A1 | 3/2009 |
| FR | 2828091 | 2/2003 |
| WO | WO 97/24989 | 7/1997 |
| WO | WO 98/17202 | 4/1998 |
| WO | WO 98/29057 | 7/1998 |
| WO | WO 99/04728 | 2/1999 |
| WO | WO 99/04728 A1 | 2/1999 |
| WO | WO 99/56665 | 11/1999 |
| WO | WO 00/18303 A1 | 4/2000 |
| WO | WO 00/41525 A2 | 7/2000 |
| WO | WO 00/41652 | 7/2000 |
| WO | WO 01/21244 A1 | 3/2001 |
| WO | WO 01/62189 | 8/2001 |
| WO | WO 01/64137 | 9/2001 |
| WO | WO 01/76510 | 10/2001 |
| WO | WO 02/41789 | 5/2002 |
| WO | WO 02/47575 | 6/2002 |
| WO | WO 02/076348 | 10/2002 |
| WO | WO 03/003943 | 1/2003 |
| WO | WO 03/094797 | 11/2003 |
| WO | 2004089253 | 10/2004 |
| WO | WO 2005/046525 | 5/2005 |
| WO | WO 2005/046525 A1 | 5/2005 |
| WO | WO 2005/065200 A2 | 7/2005 |
| WO | WO 2005/096993 A1 | 10/2005 |
| WO | 2005104957 | 11/2005 |
| WO | 2006054107 | 5/2006 |
| WO | 2006063199 | 6/2006 |
| WO | WO 2006/063199 | 6/2006 |
| WO | WO 2006/086135 A2 | 8/2006 |
| WO | 2006116558 | 11/2006 |
| WO | WO 2006/135551 A2 | 12/2006 |
| WO | WO 2006/138173 A2 | 12/2006 |
| WO | WO 2007/071436 A2 | 6/2007 |
| WO | WO 2007/076463 A2 | 7/2007 |
| WO | WO 2008/097589 A1 | 8/2008 |
| WO | WO 2008/125153 | 10/2008 |
| WO | WO 2008/125153 A1 | 10/2008 |

OTHER PUBLICATIONS

Huber et al., "Direct-Access Valve Replacement: A Novel Approach for Off-Pump Valve Implantation Using Valved Stents," Journal of the American College of Cardiology, 46(2): 366-370, Jul. 19, 2002.
U.S. Appl. No. 11/612,980, filed Dec. 19, 2006.
U.S. Appl. No. 11/612,968, filed Dec. 19, 2006.
U.S. Appl. No. 11/612,972, filed Dec. 19, 2006.
U.S. Appl. No. 11/851,523, filed Sep. 7, 2007.
U.S. Appl. No. 11/851,528, filed Sep. 7, 2007.
European Search Report and Search Opinion of European Patent Application No. 06126556.7, dated Jun. 27, 2007.
European Search Report Issued in EP Application No. 09160183, dated Oct. 2, 2009, 6 pages.
European Search Report Issued in EP Application No. 09160186, dated Oct. 6, 2009, 5 pages.
European Search Report Issued in EP Application No. 07115951, dated Sep. 24, 2009, 8 pages.
Extended European Search Report issued in EP Application 06126552, dated Jun. 6, 2007, 7 pages.
Extended European Search Report issued in EP Application 09158822, dated Sep. 9, 2009, 5 pages.
Ho, Paul C., "Percutaneous aortic valve replacement: A novel design of the delivery and deployment system", Minimally Invasive Therapy, 2008; 17:3; 190-194.
Partial European Search Report issued in EP App No. 06126556, mailed Apr. 16, 2007, 6 pages.
Extended European Search Report issued in EP Application 06126556, dated Jul. 6, 2007, 13 pages.
Extended European Search Report issued in EP Application 09158822, dated Sep. 9, 2009, 5 pages.
European Search Report and Search Opinion of European Patent Application No. 07115960.2, dated Jan. 24, 2008.
European Search Report issued in EP Application 08163752, dated Dec. 29, 2008.
European Search Report Issued in EP 09160184 dated Oct. 22, 2009.
Huber et al., "Direct-Access Valve Replacement: A Novel Approach for Off-Pump Valve Implantation Using Valved Stents", Journal for the American College of Cardiology, pp. 366-370, vol. 46, No. 2, Jul. 19, 2005, ISSN: 0735-1097/05, published on-line Jul. 5, 2005.

\* cited by examiner

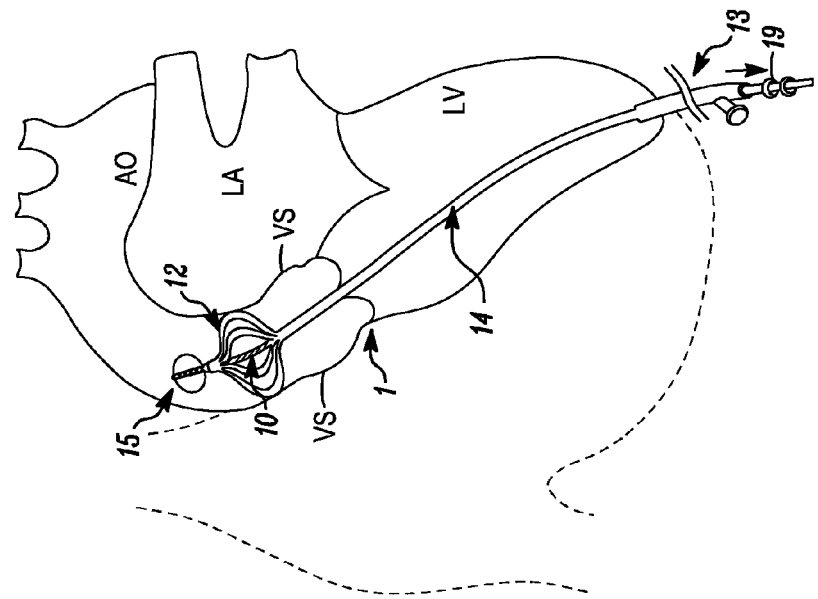
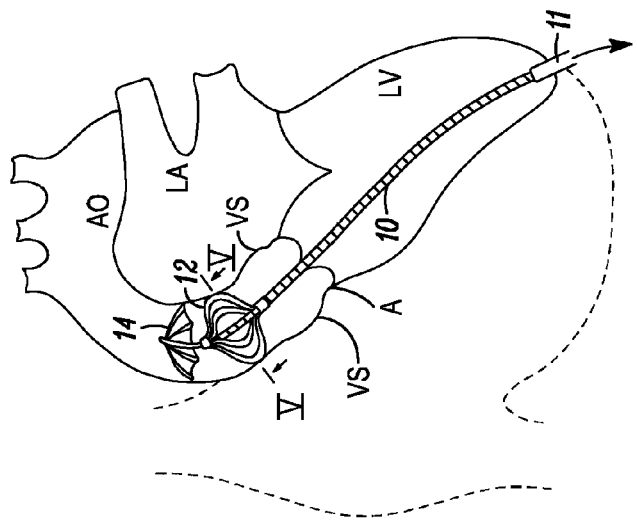
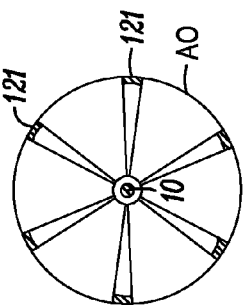

SYSTEM FOR IN SITU POSITIONING OF CARDIAC VALVE PROSTHESES WITHOUT OCCLUDING BLOOD FLOW

CROSS-REFERENCE TO RELATED APPLICATION

This application is related to co-pending U.S. application Ser. No. 11/612,972, entitled "Device for In Situ Axial and Radial Positioning of Cardiac Valve Prostheses," U.S. application Ser. No. 11/612,980, entitled "Instrument and Method for In Situ Deployment of Cardiac Valve Prostheses," and U.S. application Ser. No. 11/612,968, entitled "Device for In Situ Positioning of Cardiac Valve Prostheses," all of which were filed on even date herewith and are hereby incorporated by reference.

TECHNICAL FIELD

The present invention relates to instruments for the in situ positioning of implantable devices. In particular, the invention relates to the in situ positioning of expandable prosthetic cardiac valves.

BACKGROUND

Recently, there has been increasing consideration given to the possibility of using, as an alternative to traditional cardiac-valve prostheses, valves designed to be implanted using minimally-invasive surgical techniques or endovascular delivery (so-called "percutaneous valves"). Implantation of a percutaneous valve (or implantation using thoracic-microsurgery techniques) is a far less invasive act than the surgical operation required for implanting traditional cardiac-valve prostheses.

These expandable prosthetic valves typically include an anchoring structure or armature, which is able to support and fix the valve prosthesis in the implantation position, and prosthetic valve elements, generally in the form of leaflets or flaps, which are stably connected to the anchoring structure and are able to regulate blood flow. One exemplary expandable prosthetic valve is disclosed in U.S. Publication 2006/0178740 A1, which is incorporated herein by reference in its entirety.

An advantage of these expandable prosthetic valves is that they enable implantation using various minimally invasive or sutureless techniques. One non-limiting exemplary application for such an expandable valve prosthesis is for aortic valve replacement. Various techniques are generally known for implanting such an aortic valve prosthesis and include percutaneous implantation (e.g., transvascular delivery through a catheter), dissection of the ascending aorta using minimally invasive thoracic access (e.g., mini-thoracotomy), and transapical delivery wherein the aortic valve annulus is accessed directly through an opening near the apex of the left ventricle. Note that the percutaneous and thoracic access approaches involve delivering the prosthesis in a direction opposing blood flow (i.e., retrograde), whereas the transapical approach involves delivering the prosthesis in the same direction as blood flow (i.e., antegrade) Similar techniques may also be applied to implant such a cardiac valve prosthesis at other locations (e.g., a pulmonary valve annulus).

For the implantation of cardiac valve prostheses, it is important to check in a precise way the positioning of the various parts of the valve prosthesis. This applies to both axial positioning, to ensure that the prosthetic valve is positioned properly with respect to the valve annulus, and angular positioning, to ensure that the prosthesis may optimally engage the Valsalva sinuses, thus ensuring that the prosthetic valve leaflets are located with respect to the valve annulus at positions essentially corresponding to the positions of the natural valve leaflets.

There is a need in the art for delivery and implantation instruments capable of delivering an expandable prosthetic valve to a precise location associated with a corresponding valve annulus. There is a further need for instruments adapted to carefully control expansion of the valve to prevent the valve from misaligning during valve expansion.

SUMMARY

The present invention, according to one embodiment, is a device for use in positioning a cardiac valve prosthesis in a vessel. The device comprises a wire element to facilitate advancement of the valve prosthesis, the wire element including an abutment element configured to limit advancement of the prosthesis and an expandable element coupled to the wire element, the expandable element including an expanded configuration operable to axially secure the wire element with respect to an implantation site in the vessel, while not occluding blood flow through the vessel. The expandable element is disposed in a symmetrical fashion about the wire element, such that at least a portion of the wire element is generally positioned along a central longitudinal axis of the vessel.

The present invention, according to another embodiment, is a method of implanting a replacement aortic valve prosthesis at an implantation site. The method includes advancing a positioning instrument having an expandable element and a wire element through an aortic annulus to an anchoring position distal to the Valsalva sinuses, deploying the expandable element to secure the positioning instrument to the aortic wall, while not occluding blood flow through the aortic arch, advancing the aortic valve prosthesis over the wire element to a reference point coupled to the wire element, such that the prosthesis is in a desired position with respect to the aortic annulus, and expanding the aortic valve prosthesis, such that the prosthesis anchors to the aortic annulus and the Valsalva sinuses.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 3-12 (FIGS. 5, 7 and 9 being cross-sectional views according to the lines V-V, VII-VII and IX-IX of FIGS. 4, 6 and 8, respectively) show deployment instruments, according to various alternative embodiments of the present invention.

Figure 2:
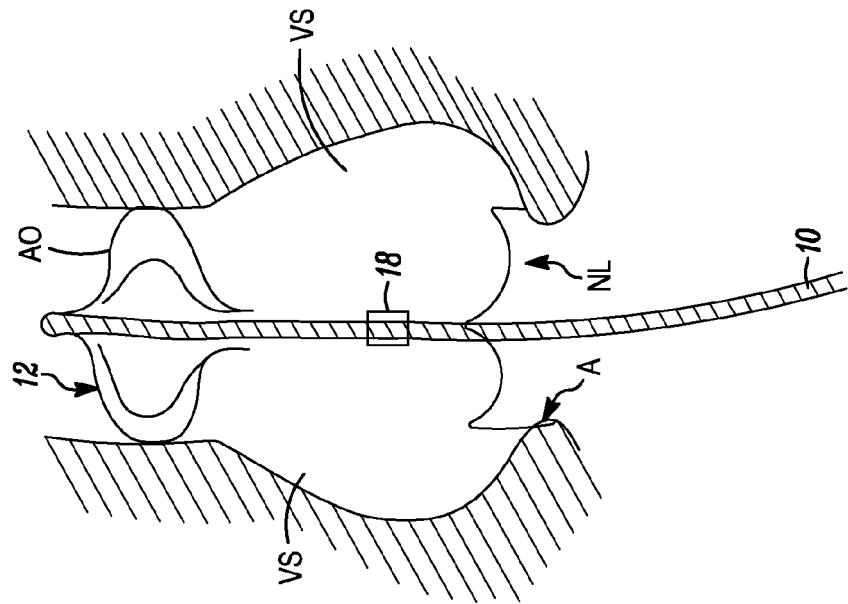
FIG. 2 is a schematic view showing the basic structure and principle of operation of a deployment instrument, according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Without limiting the scope of the invention, the description that follows makes reference to an instrument employed for the implantation of a cardiac valve prosthesis destined to replace an aortic valve. It will be apparent that the instrument of the present invention may likewise be employed in connection with implantation of valve prostheses at different locations (e.g., pulmonary valve or mitral valve).

Figure 1:
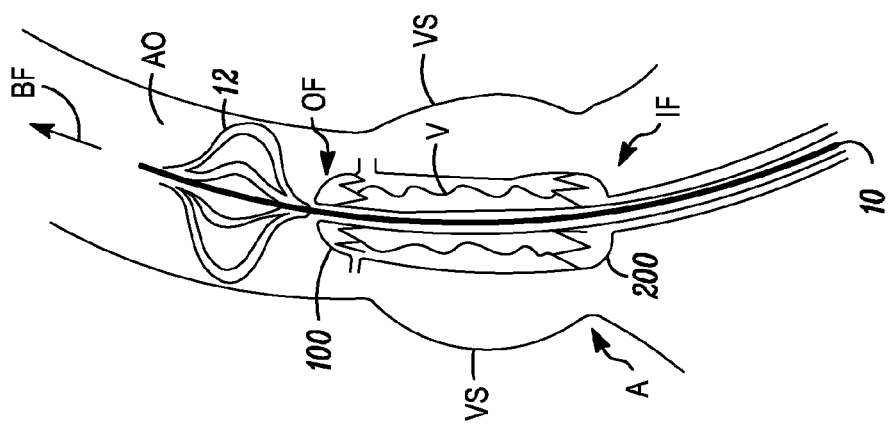
FIG. 1 is a schematic view showing the implantation of a cardiac valve prosthesis using an instrument described herein, according to one embodiment of the present invention.
Figure 9:
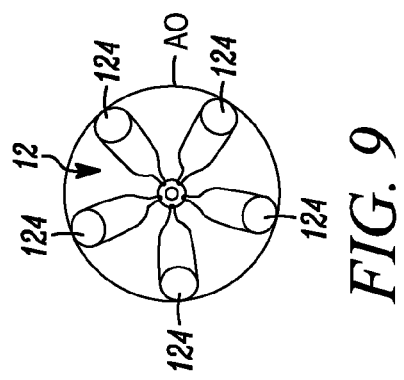
Figure 8:
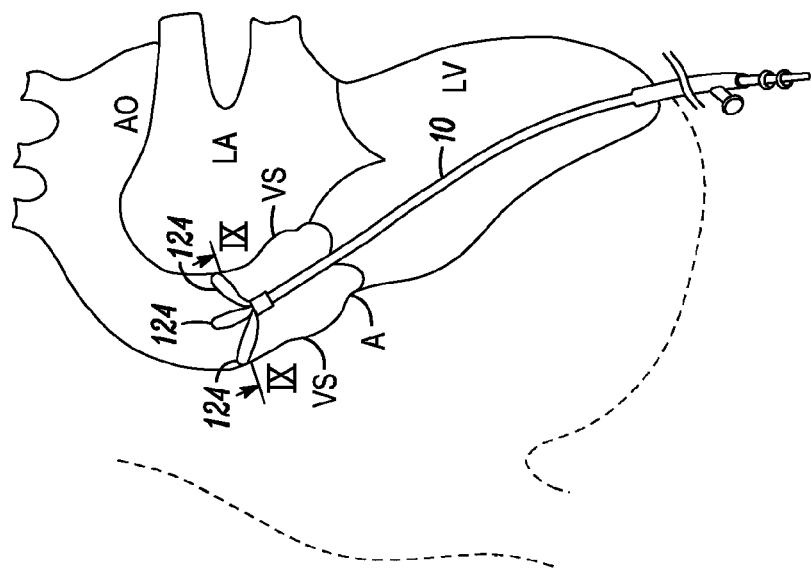

FIG. 1 is a schematic view showing the implantation of a valve prosthesis at the aortic valve location. The prosthesis V may be any of a variety of minimally-invasive or expandable cardiac valve prostheses known in the art. The prosthesis V, for example, could be of the type described in U.S. Publication 2006/0178740 A1. As shown in FIG. 1, the valve prosthesis V includes two radially expandable annular end portions, namely an inflow portion IF and an outflow portion OF. The terms "inflow" and "outflow" refer to the pulsated blood flow through the prosthesis V.

The prosthesis V is configured to be positioned with the annular inflow portion IF in correspondence with the aortic annulus A and the annular outflow portion OF located in the ascending line of the aorta AO, in a fluidodynamically distal position with respect to the Valsalva sinuses VS. The prosthesis V is provided with anchoring formations (not shown) that connect in a bridge-like fashion the annular end portions IF, OF. The anchoring formations are configured to extend into the Valsalva sinuses to anchor the valve prosthesis V in the implant position, thus helping to longitudinally secure the prosthesis V. By extending into the sinuses of Valsalva VS, which form a three-lobed cavity downstream the valve annulus, the anchoring formations (e.g., three formations disposed at roughly 120° angles from each other over about the circumference of the prosthesis V) also ensure the appropriate angular positioning of the valve prosthesis V, so that the prosthetic valve leaflets will be at angular positions corresponding to the angular positions of the natural valve leaflets with respect to the valve annulus. FIGS. 2-4, 8, and 10 schematically show the natural valve leaflets in correspondence with the valve annulus. These figures show that the instrument of the invention can be located at the implantation site before the possible ablation of the natural valve leaflets.

The prosthesis V shown in FIG. 1 is contained in a carrier portion of an instrument used for positioning and deploying the valve prosthesis V in situ. This carrier portion includes a capsule having two deployment elements 100, 200 each in the form of a collar, sheath, or cap that constrains the prosthesis V in a radially contracted position. Once the implantation site is reached, the two deployment elements 100, 200 can be displaced longitudinally so as to uncover the prosthesis V. In an embodiment wherein the prosthesis V is formed from a superelastic material, the prosthesis V is then able to radially expand upon release from the deployment elements 100, 200. One exemplary embodiment of such a deployment instrument is disclosed in co-pending, commonly-assigned U.S. application Ser. No. 11/612,980, entitled "Instrument and Method for In Situ Deployment of Cardiac Valve Prostheses," which was filed on even date herewith. In one embodiment, the prosthesis V and the deployment instrument include an axial lumen configured to accept a guide wire, such that the instrument may be advanced through a patient's vasculature over such guide wire.

As shown in FIG. 1, the instrument of the present invention includes a stylet or guide wire 10 and an expandable element 12 mounted on a distal portion thereof. As more clearly illustrated in FIG. 2, the expandable element 12 is configured to be located and expanded in the ascending portion of the aorta AO at a fluidodynamically distal position with respect to the Valsalva sinuses SV. Accordingly, the distal portion of the wire 10 can be positioned precisely with respect to the implantation site of the valve prosthesis V, in both the axial and the radial direction, with the wire 10 extending in a precise radial position (e.g. substantially central) with respect to the implantation lumen, which in the exemplary case considered herein is the aorta AO. In one embodiment, the expandable element 12 is configured to be able to expand or to swell with respect to the guide wire 10 under conditions of substantial rotational symmetry, so that, with the element 12 in an expanded condition, the distal part of the wire 10 is in a substantially central position with respect to the aortic lumen.

With respect to axial positioning, once the element 12 is disposed at a given axial position along the ascending line of the aorta, and thus at a given position with respect to the aortic annulus, the expandable element 12 serves as a reference point. The prosthesis V may thus travel along the guide wire 10 to locate it at a desired axial position, before it is anchored at the desired location with respect to the valve annulus. The present invention thus allows for precise positioning of a prosthesis V, by providing a guide for advancing the prosthesis to the implantation site.

Several variations of the expandable element 12 are contemplated. In one embodiment, once expanded, the element 12 does not undesirably obstruct blood flow (represented by the arrow designated BF in FIG. 1). In this embodiment, blood flow will not be impeded, and blood will be able to keep on flowing from the ventricle (designated LV in FIGS. 3, 4, 8 and 10) towards the aorta AO in the pulsating fashion determined by the alternate phases of systole and diastole. Accordingly, the instrument of the present invention can be used without recourse to extracorporeal circulation, with the further effect of facilitating the sequence of positioning, deployment and implantation of the prosthesis V without time constraints, which would inevitably apply if the expandable element completely obstructed the cross section of the aorta (or, in general, of the treated lumen).

In one exemplary embodiment, the expandable element 12 is a completely "apertured" structure, namely a structure that in its expanded position is traversed by passageways through which blood can readily flow. Alternatively, the non-obstructive effect can be achieved by ensuring that the element 12 has an expansion cross-sectional radius which is smaller than the cross-sectional radius of the treated lumen. In this embodiment, general centering the guide wire 10 with respect to the implantation lumen will be accomplished by the element 12 "floating" in the blood flow and will not require the expandable element 12 to apply any radial pressure against the lumen wall. This embodiment may be helpful in at least some patients suffering from degenerative diseases, as the lumen wall may be fragile and therefore susceptible to be damaged by pressure.

In one embodiment, the guide wire 10 has a stiffness sufficient to cause its length extending from the expandable element 12 towards the valve annulus to remain approximately in the center of the body lumen throughout. A distal portion of the guide wire 10, for example, has a stiffness sufficient to hold and retain its shape.

The embodiments of FIGS. 3 and 4 the expandable element 12 having a general cage-like structure. In this embodiment, the expandable element 12 includes a plurality of wire-like elements that are operable between a first position co-extensive with the guide wire 10 and a second position projecting outwardly from the guide wire. FIG. 3 shows an embodiment wherein the cage-like structure includes a portion of a tubular element (for instance of a metal tube) having a distal end fixed to the distal end of the guide wire 10 and a proximal end fixed to a sheath 11 slidably arranged over the guide wire 10.

In this embodiment, the wall of the tubular element includes a plurality of slits extending in a substantially longitudinal direction defining therebetween wire-like or band-like portions of the tube wall. According to one embodiment, these longitudinal slits are formed from a microtube using a laser cutting technique. The microtube can be of the type normally used for producing angioplasty stents (e.g., a hypotube).

These band-like expandable elements 12 may be deployed, for example, by manipulating a proximal control means 13, of a known type in the catheter art, to effect a relative movement of the guide wire 10 and the sheath 11. The sheath 11 may be advanced distally towards the expandable elements 12 to reduce the distance between the distal end of the sheath 11 and the distal end of the guide wire 10, thereby deforming the tubular elements and causing the wire-like or band-like wall elements between the slits to protrude outwardly of the guide wire 10 to form a radially expanded element 12 as desired. The further that the sheath 11 is advanced towards the distal end of the guide wire, the further that the tubular elements protrude radially.

The tubular element can be comprised of any metal material approved for use in the biomedical field, such as for instance steel, and in that case the expansion to form the expanded element 12 is positively determined by sliding the sheath 11 over the guide wire 10. The tubular elements may also be formed for example of any known polymer material approved for human implantation.

FIG. 4 shows an embodiment wherein the expandable element 12 is comprised of a cage-like structure of wires or bands 121 made from a superelastic material (for instance, Nitinol). In a "rest" condition, namely in the absence of constraints applied thereto, the wires or bands 121 will naturally assume the desired cage-like configuration of the element 12 in the expanded condition. In this embodiment, the sheath 11 extends initially to the distal end of the guide wire 10 in order to constrain to the Nitinol wires or bands 121 in a radially contracted position. When retracted along the guide wire 10 (see bottom of FIG. 4), the sheath 11 will uncover and release the wires or bands 121, which will then be free to return, because of their superelastic characteristics, to the radially expanded position, which corresponds to the desired expansion of the element 12.

The cage-like structure constituting the expandable element 12 is shown FIGS. 3 and 4 in an "onion-like" configuration, with the wire-like or band-like elements forming the cage connected at both the proximal and distal ends of the cage. In an alternative embodiment, the expandable element 12 could be configured in an "artichoke-like" shape, with the wire-like or band-like elements forming the cage spreading from the proximal extremity of the cage according to a general wine glass configuration without any connection at their distal ends.

According to one embodiment, the cage-like structure includes at least three such elements. In other embodiments, the cage-like structure includes at least five or six such elements. FIG. 5, for example, shows a one such configuration including six elements. More elements may provide more precise positioning of the guide wire 10 at the center of the treated lumen (e.g., the aorta AO). The number of elements forming the cage-like structure, as well as the choice of the constituent material and the manner of expanding the structure, are influenced by the fact that, in order to reach the desired expanded position shown in FIG. 2, the expandable element 12 must pass through the site of the aortic valve. In some situations, wherein the natural valve leaflets NL were not removed, the natural valve leaflets may be extensively calcified and thus resist penetration. Accordingly, in some situations, it is important that the expandable element 12 have an unexpanded cross sectional profile that is as small as possible, to facilitate penetration through the calcified valve leaflets.

According to one exemplary embodiment, as shown in FIG. 4, the instrument further includes a filtering element 14, which is typically located in a fluidodynamically distal position with respect to the expandable element 12. This filtering element 14, which can also be integrated into the expandable element 12, may be expanded along with the expandable element 12 to form a net that is permeable to the blood flow BF in the aorta, but will entrap and thus retain fragments of calcified formation (e.g., possibly released during the intervention), air and clots, thereby preventing these materials from flowing into the aorta.

FIG. 3 also shows an embodiment wherein the distal end portion of the guide wire 10 includes a balloon 15. The balloon 15 is typically of the inflatable type and is intended to act as a fluidodynamic dragging element, according to the principles of operation of those balloons generally known in the art as Swan-Ganz balloons. As indicated, the instrument described herein is primarily intended to be used in transapical insertion procedures, wherein the instrument is introduced in the ventricle cavity and advanced towards the aortic valve site. Once the instrument is inserted in the ventricle, the Swan-Ganz balloon 15 at the distal end portion will be carried by the blood flow during the ventricle systole and drawn to the aorta. In this way, the distal end of the instrument will be automatically drawn toward the aortic valve by the blood flow. The blood flow will then further draw the Swan-Ganz balloon 15 and the distal end of the instrument through the aortic annulus and on through the Valsalva sinuses to the ascending line of the aorta where the expandable element 12 is to be positioned. In one embodiment, the Swan-Ganz balloon 15 is configured to be selectively deflated, for instance to allow passage through heavily calcified natural valve leaflets before ablation. The entrapment element 14 and/or the Swan-Ganz balloon 15 can be optionally included with any of the embodiments disclosed herein.

Figure 6:
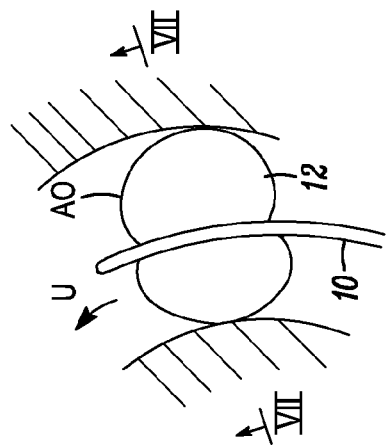
Figure 7:
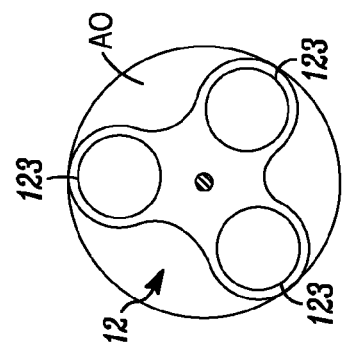

FIGS. 6-9 show expandable elements 12 in the form of inflatable balloons. Specifically, FIGS. 6 and 7 show an expandable element 12 comprising an inflatable balloons with a multi-lobed structure. In one exemplary embodiment, a balloon comprising three expandable sections 123 angularly spaced at 120° intervals about the circumference. Such a multi-lobed balloon structure, and a related manufacturing process, is described in detail in EP-A-0 512 359. In this embodiment, the various lobes 123 of the balloon, once expanded, do not obstruct the treated lumen (e.g., the aorta AO). In an alternative embodiment, shown in FIGS. 8 and 9, the expandable element 12 includes a bundle of expandable bar-like balloons 124 of the type used, for instance, for implanting angioplasty stents. Both in the case of an expandable element comprised of a multi-lobed balloon (FIGS. 6 and 7) and in the case of an expandable element including a bundle of bar-like balloons (FIGS. 8 and 9), the action of inflation (and deflation) of the expandable element 12 can be accomplished by injecting (and withdrawing) fluid through a lumen.

Figure 10:
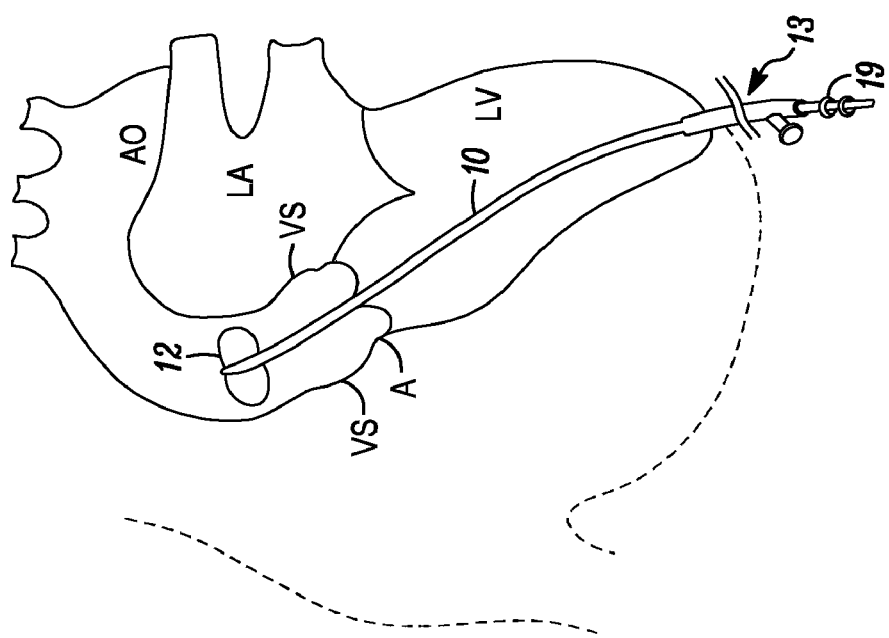

FIG. 10 shows an alternative embodiment including a single balloon. In this embodiment, the expandable element 12 can be expanded so as to occupy only part of the net cross section of the implantation lumen (e.g., the aorta AO). According to one embodiment, a substantially non-obstructive effect of the free flow of the blood in the treated lumen, which allows the expandable element 12 to remain in an expanded condition long enough to permit the implantation of a valve prosthesis V without the duration of the intervention becoming a critical parameter, is achieved if the expandable element 12, when expanded, occupies less than about 90 to 95% of the net cross sectional area of the lumen or (for elements 12 having an apertured structure with passageways for blood therethrough) the area of the circle whose radius is equal to the expansion radius of the element 12 with respect to the guide wire 10. In another embodiment, the expandable element 12 occupies less than about 75% of the net cross sectional area of the lumen.

As illustrated in FIG. 10, this non-obstructive effect on blood flow can be also achieved by an element 12 having a structure not of an apertured type by ensuring that, when expanded, the element 12 has an expansion radius smaller that than the radius of the lumen (the radius of the aorta, in the exemplary case considered herein) at the location where the element is expanded. In this way, while being still centered in a radial sense with respect to the lumen, due to fluidodynamic actions of blood flowing around it, the expandable element 12 will not exert any appreciable pressure on the lumen walls which, at least in some patients affected by particular pathologies, may be particularly sensitive and fragile.

Figure 12:
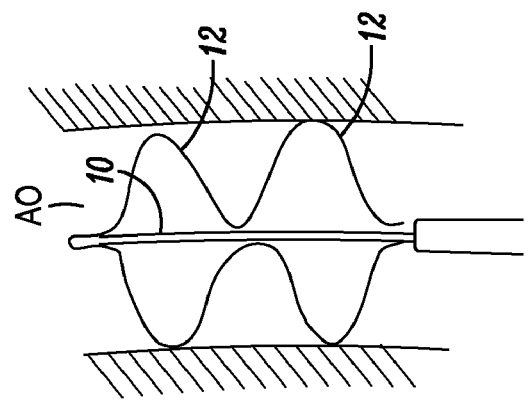
Figure 11:
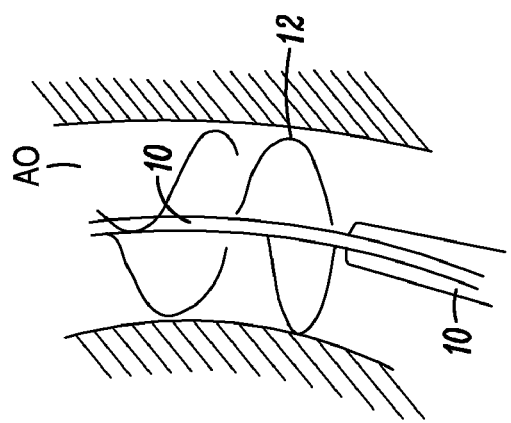

FIGS. 11 and 12 schematically show still other possible embodiments of the expandable element 12. FIG. 11, for instance, shows an expandable element 12 wherein the elements of the cage-like or shape similar to an onion-like structure do not extend along the "meridians" of the expandable structure (as is the case of FIGS. 3 and 4), but rather follow approximately helical trajectories. This solution may be advantageously used in conjunction with both self-expandable elements (e.g., Nitinol) and with elements whose expansions is obtained by a positive action (e.g., inflating a balloon or sliding a sheath 11 over the guide wire 10). According to the embodiment of FIG. 12, the guide wire 10 includes a plurality of expandable elements 12 (e.g., onion-like cage structures) arranged in a cascaded configuration and adapted to be selectively expandable in a coordinated manner.

Figure 15:
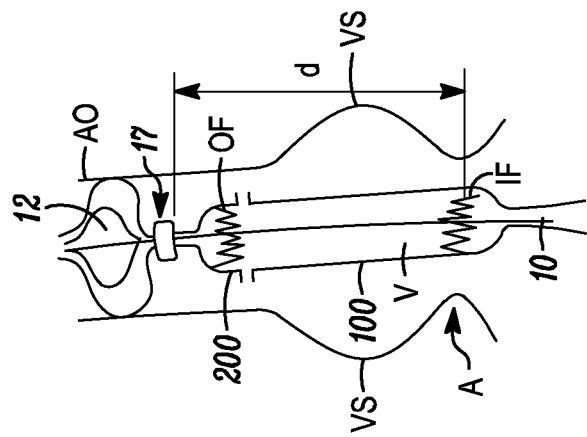
FIGS. 13-15 are schematic view showing further details of the instrument, according to various embodiments of the present invention.
Figure 14:
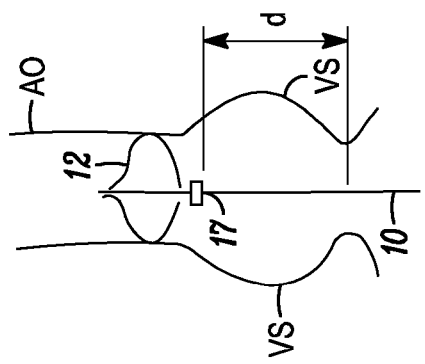
Figure 13:
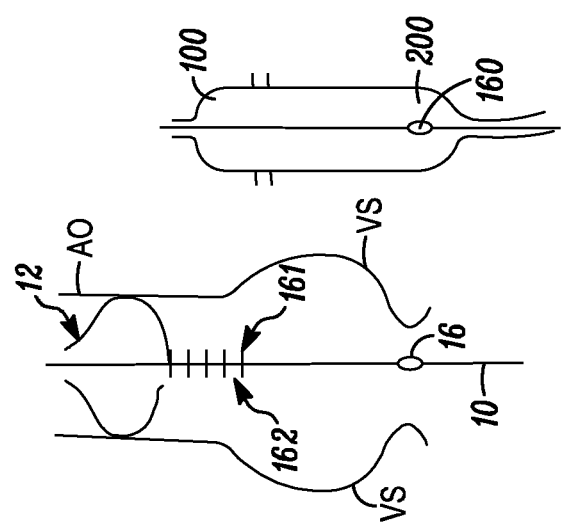

FIGS. 13-15 show how the instrument described herein may ensure the correct axial positioning of the valve prosthesis V with respect to a valve site (e.g., an aortic valve annulus). In the illustrated embodiment, the instrument is employed to ensure that the annular inflow portion IF is positioned to be deployed in appropriate correspondence with the valve annulus A.

FIG. 13 shows a solution wherein at least one opaque marker 16 is provided on the guide wire 10 (or the expandable element 12). The designation "opaque" (e.g., radiopaque) denotes any marker which is visible and can be observed to identify its position in the patient body by resorting to current imaging techniques (e.g., radioscopy and nuclear magnetic resonance). The marker 16 assists the operator to advance the instrument (the guide wire 10 and expandable element 12) through the valve annulus A so as to locate the expandable element 12 in the aorta distally with respect to the Valsalva sinuses. Specifically, the operator will be able to verify that the marker 16 has reached a clearly identified position, for instance by positioning it in the plane of the valve annulus A, about the center of the annulus.

The expandable element 12 is then expanded so that the marker 16, and thus the guide wire 10, substantially maintain the desired axial position. In the embodiment shown in FIG. 14, the axial position of the guide wire 10 can be further secured at a desired position by blocking (by means of a blocking device 19 of a known type) the proximal end of the guide wire 10 that is located outside the patient's body. This further inhibits axial movement of the guide wire 10, even in the case where the expandable element 12 is free or slightly "floating" in radial sense with respect to the aorta wall.

Positioning and securing the expandable element 12 and the guide wire 10 facilitates positioning the valve prosthesis V at the desired position with respect to the implantation site (e.g., aortic valve annulus). The results in terms of accuracy already achieved in positioning of the instrument will thus be exploited for the purpose of positioning of the valve prosthesis V.

During an implantation procedure, the valve prosthesis V is advanced longitudinally over the guide wire 10 (see FIGS. 1 and 13) until an opaque marker 160 positioned, e.g. at the inflow end IF of the valve prosthesis V aligns (e.g., overlaps) with the marker 16 on the guide wire 10, to thus ensure that the prosthesis V is in the desired position for implantation, with the inflow end IF in the plane of the valve annulus A. This technique lends itself to further refinement, both regarding the positioning of the instrument 10, 12 and the relative positioning of the valve prosthesis V with respect to the instrument previously positioned.

For instance, instead of a single marker 16, the guide wire 10 may include multiple markers 161, 162, etc. defining a graduated scale along the guide wire 10. The operator will thus be able to position the marker 160 on the valve prosthesis V in alignment with one particular marker in the scale, in view of specific requirements arising at the time of implantation.

In a complementary and dual manner, it is possible to provide multiple markers on the prosthetic valve V. These markers can be provided, rather than on the cardiac valve prosthesis V, on the respective deployment instrument, for instance on either or both the deployment elements 100, 200 mentioned above. Providing the markers on the prosthesis V allows the operator to check over time the positioning of the valve prosthesis V.

FIGS. 14 and 15 show exemplary embodiments including an abutment formation 17, which may, for instance, have the form of a collar-like member mounted on the guide wire 10 (or on the expandable element 12). The formation 17 is arranged for mechanical co-operation with the prosthesis V and/or with the distal part of the relative deployment instrument (for instance with the deployment element 200) in order to stop the sliding movement of the prosthesis V over the guide wire 10.

FIGS. 14 and 15 specifically illustrate a situation where the distal border of the deployment element 200 must be at a distance d with respect to the plane of the aortic annulus A, in order to properly locate the prosthesis V at the implant site. The guide wire 10 or expandable element 12 is thus positioned in such way that the stop element 17 is exactly located at a distance d with respect to the plane of the aortic annulus A. In this embodiment, the correct axial positioning of the prosthesis V will be easily achieved by sliding the prosthesis V over the guide wire 10 up to the point where, as schematically illustrated in FIG. 15, the distal border of the deployment element 200 abuts against the element 17 provided on the guide wire 10 (or, possibly, on the expandable element 12).

At this point, by realizing that the prosthesis V can no longer be advanced over the guide wire 10 because of the mechanical co-operation of deployment element 200 against the abutment element 17, the operator will know that the prosthesis V has reached the desired position. The operator can thus proceed to deploy the annular inflow and outflow portions IF, OF of the prosthesis V without having to worry about the axial (and radial) positioning of the prosthetic valve. The operator will thus be able to concentrate on other issues related to implanting the prosthesis, such as the appropriate angular positioning of the prosthesis V, by making sure that the protruding parts of the prosthesis V are angularly positioned in correspondence with the Valsalva sinuses and correctly extend into the Valsalva sinuses the prosthesis V is deployed.

A micrometric adjustment mechanism (of a type known by itself) actuatable from the proximal extremity of the instrument can be associated to the abutment element 17 for regulating in a precise way, if necessary, the position of the element 17 with respect to the guide wire 10 and/or the expandable element 12. This adjustment feature may turn out to be advantageous in certain situations where the expandable element 12 must be expanded and thus deployed in a different position with respect to the originally anticipated position. In this case, adjusting the position of the abutment element 17 makes it possible to position that element at the position where it would be disposed had the expandable element 12 been positioned in the anticipated way.

FIG. 2 refers to an exemplary embodiment that includes a pressure sensor 18 (e.g., piezoelectric pressure sensor). The pressure signal generated by the sensor 18 is transmitted to the outside of the body of the patient (for instance through wires that extend along the guide wire 10) and makes it possible to detect if the point where the pressure sensor 18 is located is momentarily upstream or downstream of the valve annulus A. Having such information available is a further aid to the operator in achieving the correct positioning of the instrument and, accordingly, of the valve prosthesis V. In yet another embodiment, the instrument further includes a lumen adapted to inject contrast fluid. In this embodiment, the contrast fluid may be used by the operator to obtain an image of the implantation site.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof. This is particularly true as regards the possible combination, within a single implantation kit, of the instrument described herein with a deployment instrument described in the co-pending patent application already referred to in the foregoing.

We claim:

1. A device for use in positioning a cardiac valve prosthesis at an implantation site having an aortic valve annulus, the device comprising:
a wire element operable to facilitate advancement of the valve prosthesis; and
an expandable element coupled to the wire element, the expandable element including at least three substantially longitudinal band elements formed of a superelastic material and having a cage-shaped expanded configuration, the expanded configuration operable to axially secure the wire element with respect to the implantation site in the vessel, while not occluding blood flow through the vessel;
an abutment element configured to limit advancement of the prosthesis, the abutment element coupled to the wire element and disposed at a location proximal to the expandable element such that during use the abutment element operates to axially align the prosthesis with the aortic valve annulus; and a filter element couple to the wire element at a location distal to the abutment element, the filter element configured such that it is permeable to blood flow;
wherein the expandable element is disposed in a symmetrical fashion about the wire element, configured such that during use at least a portion of the wire element is generally positioned along a central longitudinal axis of the vessel.

2. The device of claim 1 wherein the cardiac valve prosthesis is an aortic valve prosthesis.

3. The device of claim 2 further including at least one reference element to facilitate relative positioning of the cardiac valve prosthesis with respect to an implantation site.

4. The device of 3 wherein the expandable element is made from a superelastic, self-expanding material and has a generally cage-like configuration.

5. A device for use in positioning a cardiac valve prosthesis in a vessel, the device comprising a wire element coupled to an expandable element, wherein the expandable element includes at least three substantially longitudinal band elements formed from a superelastic material, the band elements defining an expanded configuration operable to axially secure the wire element with respect to an implantation site in the vessel, while not occluding blood flow through the vessel, the wire element further having an abutment element configured to limit advancement of the prosthesis and disposed at a location proximal to the expandable element, such that during use the abutment element operates to axially align the prosthesis at the implantation site the wire element further having a filter element coupled to the wire element at a location distal to the abutment element, the filter element configured such that it is permeable to blood flow.

6. The device of claim 5 wherein the expandable element is configured to expand symmetrically about the wire element, such that in the expanded configuration the wire element is disposed substantially in a longitudinal center of the lumen.

7. The device of claim 5 wherein the expandable element has a generally cage-like expanded configuration.

8. The device of claim 7 wherein the expandable element is formed from a tubular body having generally parallel slits disposed about its circumference, and further comprising a catheter slidable over the wire element to compress the tubular body thereby causing the expandable element into the expanded configuration.

9. The device of claim 5 wherein the expandable element is made from a superelastic, self-expanding material.

10. The device of claim 5 wherein the expandable elements include a plurality of structures located along the wire element.

11. The device of claim 5 further including at least one reference structure coupled to the wire element to enable positioning of the valve prosthesis with respect to the implantation site.

12. The device of claim 11 wherein the reference structure is a radiopaque marker.

13. The device of claim 11 wherein the reference structure is an abutment coupled to the wire element at a selectively adjustable position with respect to the implantation site.

* * * * *